United States Patent [19]

Detwiler

[11] Patent Number: 5,416,004
[45] Date of Patent: May 16, 1995

[54] MULTILAYER ANALYTICAL ELEMENT CONTAINING PRIMARY AMINE BUFFER AND METHOD FOR THE DETERMINATION OF ETHANOL

[76] Inventor: Richard L. Detwiler, Eastman Kodak Company, Rochester, N.Y. 14650-2201

[21] Appl. No.: 5,683

[22] Filed: Jan. 19, 1993

[51] Int. Cl.$^6$ .................... C12Q 1/26; G01N 21/00; G01N 33/00; G01N 21/77

[52] U.S. Cl. ........................... 435/26; 435/25; 435/14; 435/4; 422/56; 422/60; 422/68.1; 436/132; 436/131; 436/170; 436/164

[58] Field of Search .............. 435/26, 25, 16, 17, 435/14, 4; 436/170, 132, 131, 164; 422/56, 60, 68.1

[56] References Cited

U.S. PATENT DOCUMENTS

| | | | |
|---|---|---|---|
| 3,493,467 | 2/1970 | Drell et al. | 435/26 |
| 3,926,736 | 12/1975 | Bucolo | 435/26 |
| 3,941,659 | 3/1976 | Koch et al. | 435/26 |
| 3,992,158 | 11/1976 | Przybylowicz et al. | 435/26 |
| 4,042,335 | 8/1977 | Clement | 435/26 |
| 4,132,528 | 1/1979 | Eikenberry et al. | 422/57 |
| 4,144,305 | 3/1979 | Cottrell, Jr. et al. | 264/247 |
| 4,258,001 | 3/1981 | Pierce et al. | 422/56 |
| 4,292,272 | 9/1981 | Kitajima et al. | 422/57 |
| 4,430,436 | 2/1984 | Koyama et al. | 422/56 |
| 4,490,465 | 12/1984 | Limbach et al. | 435/14 |
| 4,781,890 | 11/1988 | Arai et al. | 422/56 |
| 4,810,633 | 3/1989 | Bauer et al. | 435/25 |
| 4,900,665 | 2/1990 | Terashima et al. | 422/56 |
| 4,937,047 | 6/1990 | Kobayashi et al. | 435/17 |
| 5,023,052 | 6/1991 | Nagatomo et al. | 435/7.92 |
| 5,028,528 | 7/1991 | Frickey et al. | 422/56 |
| 5,047,322 | 9/1991 | Emmons et al. | 435/7.4 |
| 5,118,472 | 6/1992 | Tanaka et al. | 422/56 |

FOREIGN PATENT DOCUMENTS

| | | |
|---|---|---|
| 0264079A3 | 4/1988 | European Pat. Off. . |
| 0464942 | 6/1991 | European Pat. Off. . |
| 0464942A1 | 1/1992 | European Pat. Off. . |

*Primary Examiner*—Michael G. Wityshyn
*Assistant Examiner*—Louise N. Leary

[57] ABSTRACT

A multilayer analytical element has been prepared for accurate and rapid colorimetric determination of ethanol in aqueous specimens using alcohol dehydrogenase and an oxidized nicotinamide coenzyme. The element includes three reagent layers beneath a porous spreading layer. The middle reagent layer has a crosslinked hydrophilic binder, while the other two reagent layers have uncrosslinked binders. In addition, both uncrosslinked reagent layers include a relatively high amount of a buffer having a primary amine, which buffer maintains the layer pH at from about 8 to about 10. Alcohol dehydrogenase is in the reagent layer next to the porous spreading layer.

13 Claims, No Drawings

MULTILAYER ANALYTICAL ELEMENT CONTAINING PRIMARY AMINE BUFFER AND METHOD FOR THE DETERMINATION OF ETHANOL

FIELD OF THE INVENTION

This invention relates to clinical chemistry. In particular, it relates to a multilayer analytical element and method for the quantitative determination of ethanol.

BACKGROUND OF THE INVENTION

Ethanol is a commonly encountered toxic substance. Methods for qualitative and quantitative determination of ethanol in body fluids, particularly human body fluids, are used in medicine and in law enforcement. In medicine, the level of ethanol in the blood is significant in diagnosing liver malfunction and alcoholism, as well as for understanding the reason for an emergency room patient being comatose. In law enforcement, such assays are used to determine whether or not an automobile operator is driving under the influence of alcohol.

Ethanol testing can be accomplished using both enzymatic and nonenzymatic assays. The nonenzymatic assays have a number of disadvantages and are being widely replaced by enzymatic assays which are more accurate, highly specific, more sensitive and require less expensive procedures. Enzymatic assays are generally based on the use of alcohol dehydrogenase to catalyze the reaction of ethanol to acetaldehyde. This reaction can be used alone, or in combination with other reactions to produce a spectrophotometric signal which can be related to the amount of ethanol in the tested specimen.

One enzymatic assay is based on the direct measurement of the reduced coenzyme (NADH), such as that described in U.S. Pat. No. 3,926,736 (Bucolo). This assay is carried out entirely in solution.

Another enzymatic assay is described in EP-A-0 464 942 (published Jan. 1, 1992) which uses nicotinamide adenine dinucleotide (AND+) as a coenzyme with alcohol dehydrogenase to produce the reduced form of the coenzyme. The coenzyme, in turn, reacts with a tetrazolium salt to produce a detectable dye. The described assay is carried out in a multilayer analytical element containing tris(hydroxymethyl)aminomethane buffer and both crosslinked and uncrosslinked gelatin layers.

One problem that has been encountered in developing a dry analytical element for the assay of ethanol is the strong interference by fluoride ion present in human serum. Fluoride ion is commonly used as a preservative in serum, and interferes in assays possibly by altering the equilibrium between ethanol and acetaldehyde, and causes the assay results to be biased positively compared to the true value of ethanol in the specimen.

There is a great need for a sensitive and accurate assay for ethanol which can be carried out using an analytical element, which assay is not affected by fluoride ion.

SUMMARY OF THE INVENTION

The problem with fluoride ion interference in assays using analytical elements is overcome with an analytical element for the determination of ethanol comprising a support having thereon, in order and in fluid contact:

a) a first reagent layer containing a buffer having a primary amine mixed with an uncrosslinked hydrophilic binder, the buffer maintaining the pH at from about 8 to about 10 during an assay for ethanol and being present in an amount of at least about 25 mmoles/m$^2$, b) a second reagent layer comprising a crosslinked hydrophilic binder, c) a third reagent layer comprising alcohol dehydrogenase and a buffer present in an amount of at least about 25 mmoles/m$^2$ mixed with an uncrosslinked hydrophilic binder, the buffer being the same as that in the first reagent layer and maintaining the pH at from about 8 to about 10, and d) a porous spreading layer containing an oxidized nicotinamide coenzyme.

This invention also provides a method for the detection of ethanol comprising:

A) contacting an aqueous fluid suspected of containing ethanol with the analytical element described above, and B) detecting the absorbance of the reduced form of the nicotinamide coenzyme as an indication of the presence of ethanol in the aqueous fluid.

The present invention provides a dry analytical element for the effective and specific detection of ethanol in a relatively short time using a signal generated by the reduction of a nicotinamide coenzyme by alcohol dehydrogenase. Interference by fluoride ion is greatly reduced in assays using the element of this invention. Fluoride interference is reduced by using a high amount of a buffer which has a primary amine. Moreover, in order to use a high amount of buffer, it became necessary to put it into more than one reagent layer. Yet if the hardener typically used to crosslink the binder in standard reagent layers contacts the buffer, binder crosslinking is adversely affected. Also, the hardener also must be kept isolated from the alcohol dehydrogenase. The present invention accommodates all of these requirements with a series of three reagent layers beneath the porous spreading layer. Two reagent layers on either side of a middle reagent layer contain uncrosslinked binders and contain specific amounts of the needed buffer. The middle reagent layer is crosslinked, but contains no buffer.

DETAILED DESCRIPTION OF THE INVENTION

The element of this invention can be used to determine (that is, detect either the presence, amount or both) ethanol in biological fluids of animals or humans, but preferably in humans. Such fluids include, but are not limited to, whole blood, plasma, sera, lymph, bile, urine, semen, cerebral spinal fluid, spinal fluid, sputum, perspiration, synovial fluid, lacrimal fluid and stool specimens as well as other biological fluids readily apparent to one skilled in the art. Fluid preparations of tissues can also be assayed. Preferably, human serum is assayed with this invention.

In its broadest embodiment, the dry element of this invention has an inert support with three reagent layers and a porous spreading layer disposed thereon. The support is generally dimensionally stable, inert to chemical reaction and preferably transparent (that is, radiation transmissive for wavelengths between about 200 and 900 nm). However, non-transparent supports can be used if the mode of detection is reflectance spectroscopy instead of transmission spectroscopy. Useful supports are well known in the art, and include but are not limited to polyesters, papers, metal foils and polystyrene, polycarbonates and cellulose esters.

The porous spreading zone is prepared from any of the known materials used for such zones as described, for example in U.S. Pat. No. 4,292,272 (Kitajima et al), U.S. Pat. No. 3,992,158 (Przybylowicz et al), U.S. Pat. No. 4,258,001 (Pierce et al) U.S. Pat. No. 4,430,436 (Koyama et al), and JP 57(1982)-101760 (published Jun. 24, 1982). It is desired that the spreading zone be isotropically porous, meaning that the porosity is the same in each direction in the zone as caused by interconnected spaces or pores between particles, fibers or polymeric strands.

Preferred spreading zones are those described in U.S. Pat. No. 3,992,158 as "blush polymer" zones. Such zones can be formed on a supporting material by dissolving a polymer in a mixture of two organic liquids, one of which is a lower boiling, good solvent for the polymer and other being a high boiling, non-solvent or poor solvent for the polymer. The resulting polymer formulation is coated on the supporting material and dried under controlled conditions to leave an isotropically porous zone. Various polymers are known to be useful in this context including, but not limited to, polycarbonates, polyamides, polyurethanes and cellulose esters such as cellulose acetate (which is preferred).

Within the porous zone can be incorporated particulate materials of various sizes to enhance the void volume. Useful particulate materials include, but are not limited to, inorganic pigments such as titanium dioxide, barium sulfate, zinc oxide and lead oxide, with barium sulfate and titanium dioxide being preferred. Further details of the preparation of "blush polymers" are described in U.S. Pat. No. 3,992,158 (noted above).

The elements have at least three other layers which can contain one or more reagents needed for the assay. All of the layers are generally in fluid contact with each other, meaning that fluids, reagents and reagent products can pass or be transported between superposed regions of adjacent layers, unless of course, a reagent is immobilized in some manner so it will not migrate within or without a layer.

The reagent layers can be composed of one or more hydrophilic binder materials [such as gelatin and other colloidal materials, hydrophilic polymers such as poly(-vinyl alcohol), acrylamide polymers, vinylpyrrolidone polymers and others known in the art, or mixtures thereof] in which reagents are incorporated. The same or different (or mixtures) binders can be in the noted reagent layers. The hydrophilic binder in the first and third reagent layers is uncrosslinked, while the hydrophilic binder in the second reagent layer is crosslinked using a conventional hardener such as bis(vinylsulfonylmethyl)ether, bis(vinylsulfonyl)methane, glutaraldehyde, succinaldehyde and others known in the art using conventional amounts and procedures. Various materials for such layers are described, for example, in U.S. Pat. No. 4,042,335 (Clement), U.S. Pat. No. 4,132,528 (Eikenberry et al) and U.S. Pat. No. 4,144,305 (Figueras).

The buffer used in the first and third reagent layers is one which has a primary amine and maintains the pH of the layer during an assay at from about 8 to about 10, and preferably at from about 8.5 to about 9. A number of such buffers are known and commercially available. They include, but are not limited to, tris(hydroxymethyl)aminomethane, tris(methyl)aminomethane, and their acid forms (for example, acid addition salts of HCl, HF and the like), and tris(hydroxymethyl)aminomethane glutamate. Tris(hydroxymethyl)aminomethane or tris(hydroxymethyl)-aminomethane hydrofluoride is preferred.

The amount of buffer in each reagent layer is generally at least about 25 mmoles/m$^2$, and from about 30 to about 50 mmoles/m$^2$ is preferred. It is not necessary, but it is preferred, that the amounts in the two layers be the same. For the preferred buffers, the preferred amount in each layer is about 31 mmoles/m$^2$ which corresponds to about 3.75 g/m$^2$.

The third reagent layer also contains alcohol dehydrogenase which can be obtained from a number of commercial sources. Generally, the enzyme is present in an amount of from about 5000 to about 30,000 I.U./m$^2$. As used in this application, one I.U. represents the International Unit for enzyme activity and is defined as the amount of enzyme activity required to catalyze the conversion of 1 micromole of substrate per minute under standard pH and temperature conditions. For alcohol dehydrogenase, the standard conditions are 25° C. and a pH of about 8.

Within the porous spreading layer is an oxidized nicotinamide coenzyme which can be reduced to provide a detectable colorimetric signal upon reaction with ethanol as catalyzed by alcohol dehydrogenase. Useful oxidized coenzymes include, but are not limited to, oxidized nicotinamide adenine dinucleotide (AND+) and oxidized nicotinamide adenine dinucleotide phosphate (NADP+). For example, in the assay, NADH absorbs at about 340 nm, and NADPH absorbs at about 340 nm.

Optionally, but preferably, the porous spreading layer is separated from the three reagent layers with a hydrophilic subbing layer composed of one or more suitable hydrophilic binder materials. Such materials include, but are not limited to gelatin and other colloidal materials, polymers of vinyl pyrrolidone, vinyl alcohol, acylamide, N-alkylsubstituted acrylamide (such as N-isopropylacrylamide), including copolymers thereof, and other materials readily apparent to one skilled in the art.

One or more layers of the element can also contain one or more useful materials, such as antioxidants, coating aids, surfactants, bacteriostats and other materials known in the art to facilitate coating of the layers and fluid spreading during the assay.

A variety of different elements, depending upon the method and equipment for assay, can be prepared in accordance with this invention. They can be configured in a variety of forms and shapes, including elongated tapes of any desired width, sheets, slides or chips. Preferred elements are configured as test slides like those commercially available under the EKTACHEM ™ trademark for a variety of clinical assays. Such test slides are described in a considerable number of patents and other publications. Generally, the layers are formed on a suitable support by applying specific aqueous or solvent-based formulations of individual layer compositions in sequence using suitable coating equipment, and procedures followed by drying.

In a preferred embodiment, a multilayer analytical element of this invention comprises a nonporous, transparent support having thereon, in order and in fluid contact:

a first reagent layer containing a buffer having a primary amine as defined above mixed with an uncrosslinked hydrophilic binder, a second reagent layer comprising a crosslinked hydrophilic binder, a third reagent layer comprising alcohol dehydrogenase and the same buffer as described for the first reagent layer mixed in an uncrosslinked hydrophilic binder, a hydrophilic subbing layer, and a porous spreading layer containing an oxidized nicotinamide coenzyme.

The assay of this invention can be manual or automated. In general, the element is used by physically contacting it with the test specimen (for example, from 1 to 200 μl) suspected of containing ethanol under ambient conditions (although other temperatures can be used). The specimen and reagents become mixed within the layers of the element and any ethanol present in the specimen reacts with the oxidized nicotinamide coenzyme to produce the reduced form which is detectable as described above. Contact can be achieved in any suitable manner, for example by dipping or immersing the element into the specimen or preferably, by spotting the specimen onto the element by hand, machine or suitable dispensing means.

After specimen application, the element is exposed to any conditioning, such as incubation, heating or otherwise, that may be desirable to quicken or otherwise facilitate obtaining a test result.

Generally within about 5 minutes, a spectrophotometric measurement is made. This measurement can be made using suitable reflection or transmission spectrophotometric equipment and procedures as a measure of ethanol concentration in the test sample. Generally, the detectable signal is measured at a wavelength in the range of from about 320 to about 360 nm.

The following examples are included to illustrate the practice of this invention, and are not meant to be limiting in any way. The materials used in the examples were obtained as follows:

ESTANE ™ 5715 polyurethane resin from B. F. Goodrich, TRITON ™ X-100 and TRITON ™ X-405 nonionic surfactants and TRITON ™ X-200E anionic surfactant from Rohm and Haas (rights now owned by Union Carbide), and the remainder of the materials from Eastman Kodak Company or other commercial sources, or they were prepared using standard procedures and readily available starting materials.

EXAMPLE 1

Preferred Analytical Element for Ethanol Determination

The preferred element of this invention and amounts of components (as coated) are illustrated in the structure:

|  | Dry Coverage (g/m$^2$) |
|---|---|
| Spreading Layer | |
| Barium sulfate | 105 |
| Cellulose acetate | 8 |
| ESTANE ™ 5715 polyurethane | 1.1 |
| TRITON ™ X-405 nonionic surfactant | 2.1 |
| NAD+ | 8 |
| Subbing Layer | |
| Poly(N-isopropylacrylamide) | 0.4 |
| Third Reagent Layer | |
| Gelatin (unhardened) | 6 |
| Tris(hydroxymethyl)-aminomethane | 5 |

|  | Dry Coverage (g/m$^2$) |
|---|---|
| -continued | |
| Ottasept | 0.02 |
| TRITON ™ X-200E anionic surfactant | 0.01 |
| TRITONT ™ X-100 nonionic surfactant | 0.02 |
| Alcohol dehydrogenase | 10,000* |
| Bovine Serum Albumin | 1.75 |
| Second Reagent Layer | |
| Gelatin | 1.1 |
| Bis(vinylsulfonylmethyl) ether | 0.14 |
| TRITON ™ X-200E anionic surfactant | 0.01 |
| TRITON ™ X-100 nonionic surfactant | 0.02 |
| Ottasept | 0.003 |
| First Reagent Layer | |
| Gelatin | 6 |
| TRITON ™ X-100 nonionic surfactant | 0.02 |
| TRITON ™ X-200E anionic surfactant | 0.01 |
| Ottasept | 0.02 |
| Tris(hydroxymethyl)amino-methane | 5 |
| Poly(ethylene terephthalate) Support | |

*I.U./m$^2$

EXAMPLE 2

Determination of Ethanol

This example demonstrates the use of the element of this invention and shows the reduction of interference by fluoride ion achieved by the practice of this invention.

Interference by fluoride ion was evaluated by using serum specimens containing known amounts of ethanol. To portions of the specimens, certain quantities of sodium fluoride were added. The amount of ethanol was then determined in both a portion of the specimen containing no fluoride ion (identified as a "blank"), and in the portion of the specimen containing the fluoride ion. The difference between the two results of predicted values of ethanol concentration is then defined as the interference caused by fluoride ion.

In this particular experiment, specimens containing 60, 130 and 220 mg/dl of ethanol, respectively, were used. To a portion of each specimen was added 2000 mg/dl of sodium fluoride. Each specimen portion was assayed using analytical elements like that of Example 1 except the amount of buffer and pH were varied. The results of the assays are shown below in the table. They indicate that interference by fluoride ion is reduced by increasing pH, increasing the amount of buffer, or both.

|  | Difference in Predicted Ethanol Values (mg/dl) | |
|---|---|---|
| Amount of Ethanol (mg/dl) | pH 8.25 | pH 8.75 |
| 60 | | |
| 82 mmoles/m$^2$ buffer* | 1.7 | −1.6 |
| 49.2 mmoles/m$^2$ buffer* | 3.7 | 1.7 |
| 130 | | |
| 82 mmoles/m$^2$ buffer* | 10.4 | 3.6 |
| 49.2 mmoles/m$^2$ buffer* | 16.1 | 9.8 |
| 220 | | |
| 82 mmoles/m$^2$ buffer* | 17.0 | 7.2 |

-continued

| Amount of Ethanol (mg/dl) | Difference in Predicted Ethanol Values (mg/dl) | |
| --- | --- | --- |
|  | pH 8.25 | pH 8.75 |
| 49.2 mmoles/m² buffer* | 30.0 | 16.5 |

*Buffer = tris(hydroxymethyl)aminomethane.

The invention has been described in detail with particular reference to preferred embodiments thereof, but it will be understood that variations and modifications can be effected within the spirit and scope of the invention. All patents, patent applications (published or unpublished, domestic or foreign), journal literature, books and other published prior art cited herein are incorporated herein by reference for the teaching therein pertinent to this invention.

I claim:

1. An analytical element for the determination of ethanol comprising a support having thereon, in order and in fluid contact:
   a) a first reagent layer containing a buffer having a primary amine mixed with an uncrosslinked hydrophilic binder, said buffer maintaining the pH at from about 8 to about 10 during an assay for ethanol and being present in an amount of at least about 25 mmoles/m²,
   b) a second reagent layer comprising a crosslinked hydrophilic binder,
   c) a third reagent layer comprising alcohol dehydrogenase and a buffer present in an amount of at least about 25 mmoles/m² mixed with an uncrosslinked hydrophilic binder, said buffer being the same as that in said first reagent layer and maintaining the pH at from about 8 to about 10, and
   d) a porous spreading layer containing an oxidized nicotinamide coenzyme.

2. The element of claim 1 wherein said hydrophilic binder in each of said reagent layers is gelatin.

3. The element of claim 1 wherein said buffer in said first and third reagent layers is tris(hydroxymethyl)aminomethane, tris(methyl)aminomethane and their acid forms or tris(hydroxymethyl)aminomethane glutamate.

4. The element of claim 1 wherein said buffer in said first and third reagent layers is tris(hydroxymethyl)aminomethane or tris(hydroxymethyl)aminomethane hydrofluoride.

5. The element of claim 1 wherein said porous spreading layer is formed from a blush polymer.

6. The element of claim 1 further comprising a subbing layer between said third reagent layer and said porous spreading layer.

7. The element of claim 1 wherein said nicotinamide coenzyme is nicotinamide adenine dinucleotide.

8. The element of claim 1 wherein the amount of buffer in each of said first and third reagent layers is from about 30 to about 50 mmoles/m².

9. A method for the detection of ethanol comprising:
   A) contacting an aqueous fluid suspected of containing ethanol with an analytical element comprising a support having thereon, in order and in fluid contact:
      a) a first reagent layer containing a buffer having a primary amine mixed with an uncrosslinked hydrophilic binder, said buffer maintaining the pH at from about 8 to about 10 during an assay for ethanol and being present in an amount of at least about 25 mmoles/m²,
      b) a second reagent layer comprising a crosslinked hydrophilic binder,
      c) a third reagent layer comprising alcohol dehydrogenase and a buffer present in an amount of at least about 25 mmoles/m² mixed with an uncrosslinked hydrophilic binder, said buffer being the same as that in said first reagent layer and maintaining the pH at from about 8 to about 10, and
      d) a porous spreading layer containing an oxidized nicotinamide coenzyme, and
   B) detecting the absorbance of the reduced form of said nicotinamide coenzyme as an indication of the presence of ethanol in said aqueous fluid.

10. The method of claim 9 wherein the detecting step B) is carried out within about 5 minutes of the contacting step A).

11. The method of claim 9 wherein said aqueous fluid is human whole blood, serum or plasma.

12. The method of claim 9 wherein ethanol is detected from measuring the absorbance of the reduced form of nicotinamide adenine dinucleotide.

13. The method of claim 9 wherein during which said element is maintained at a pH of from about 8.5 to about 9.

* * * * *